US010239901B2

(12) United States Patent
Bigi et al.

(10) Patent No.: US 10,239,901 B2
(45) Date of Patent: Mar. 26, 2019

(54) PROCESSES FOR PRODUCING ORGANOPHOSPHOROUS COMPOUNDS

(71) Applicant: Dow Technology Investments LLC, Midland, MI (US)

(72) Inventors: Marinus A. Bigi, Freeport, TX (US); Michael A. Brammer, Freeport, TX (US); Glenn A. Miller, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/752,413

(22) PCT Filed: Sep. 7, 2016

(86) PCT No.: PCT/US2016/050485

§ 371 (c)(1),
(2) Date: Feb. 13, 2018

(87) PCT Pub. No.: WO2017/058476

PCT Pub. Date: Apr. 6, 2017

(65) Prior Publication Data

US 2019/0002486 A1 Jan. 3, 2019

Related U.S. Application Data

(60) Provisional application No. 62/235,090, filed on Sep. 30, 2015.

(51) Int. Cl.
*C07F 9/6574* (2006.01)
*B01D 9/00* (2006.01)

(52) U.S. Cl.
CPC ........ *C07F 9/65746* (2013.01); *B01D 9/0054* (2013.01)

(58) Field of Classification Search
CPC .......................... C07F 9/65746; B01D 9/0054
USPC ........................................................... 558/78
See application file for complete search history.

(56) References Cited

U.S. PATENT DOCUMENTS

| | | | |
|---|---|---|---|
| 3,755,393 | A | 8/1973 | Kniese et al. |
| 4,116,926 | A | 9/1978 | York |
| 4,143,075 | A | 3/1979 | Bryant |
| 4,769,498 | A | 9/1988 | Billig et al. |
| 5,235,113 | A | 8/1993 | Sato et al. |
| 5,763,670 | A | 6/1998 | Billig et al. |
| 5,763,677 | A | 6/1998 | Bryant et al. |
| 6,831,035 | B2 | 12/2004 | Puckette et al. |
| 6,906,225 | B2 | 6/2005 | Puckette et al. |
| 6,946,580 | B2 | 9/2005 | Banister et al. |
| 6,995,292 | B2 | 2/2006 | Tolleson et al. |
| 7,345,185 | B2 | 3/2008 | Ortmann et al. |
| 7,629,484 | B2 | 12/2009 | Ritter |
| 7,767,861 | B2 | 8/2010 | Ortmann et al. |
| 8,110,709 | B2 | 2/2012 | Papp et al. |
| 2004/0102658 | A1 | 5/2004 | Brown et al. |
| 2011/0130595 | A1 | 6/2011 | Lueken et al. |
| 2013/0225849 | A1 | 8/2013 | Berens et al. |
| 2017/0240578 | A1 | 8/2017 | Phillips et al. |

FOREIGN PATENT DOCUMENTS

| | | | |
|---|---|---|---|
| WO | 1997/020796 | A1 | 6/1997 |
| WO | 2002/020451 | A1 | 3/2002 |
| WO | 2007/109005 | A2 | 9/2007 |
| WO | 2013/066712 | | 5/2013 |
| WO | 2013/098370 | | 7/2013 |

OTHER PUBLICATIONS

PCT/US2016/050485, International Search Report and Written Opinion dated Nov. 29, 2016.
PCT/US2016/050485, International Preliminary Report on Patentability dated Apr. 12, 2018.

*Primary Examiner* — Kristin A Vajda

(57) ABSTRACT

The present invention relates to processes for producing organophosporous compositions having low acid content as well as processes for reprocessing partially degraded organophosporous compositions that contain high levels of phosphorous acid. In one embodiment, a process comprises: (a) receiving a solid organophosphite compound that has been recrystallized or triturated, wherein the solid organophosphite compound comprises phosphorous acid; (b) dissolving the solid organophosphite compound in an organic solvent; (c) treating the solution with a weakly basic adsorbent; and (d) collecting the treated organophosphite solution, wherein the acid content of the organophosphite following step (d) is 30 ppm or less.

15 Claims, No Drawings

PROCESSES FOR PRODUCING ORGANOPHOSPHOROUS COMPOUNDS

FIELD

The disclosure in general relates to organophosphorous compositions that are stable during long-term storage and to processes for producing organophosporous compositions having low acid content as well as processes for reprocessing partially degraded organophosporous compositions that contain high levels of phosphorous acid.

Introduction

Organophosphites and polyorganophosphites have been used for a variety of applications including as preservatives (e.g., antioxidants) for plastic materials and as ligands for homogeneous catalysis. However, maintaining the stability of phosphite ligands can be problematic. To be effective, the ligand and related catalyst must be stable under reaction conditions. The stability of the ligand can be negatively impacted by impurities, especially those that accumulate in the ligand during storage.

For example, acidic byproducts are known to cause hydrolytic degradation of phosphites, and thus require particular attention. These acidic impurities include partially hydrolyzed phosphites, phosphorous acid, and phosphoric acid formed either during organophosphite production or storage. A number of schemes have been developed to mitigate acids such as water extraction and/or the use of excess amines (e.g, triethylamine or pyridine as in U.S. Pat. No. 5,235,113). Many such approaches involve the removal of acids and/or acid salts produced during the production of the phosphite rather than during storage due to degradation.

U.S. Patent Pub. No. 2013/0225849 discloses the use of trace amounts of sodium methoxide as an additive in a washing step during the purification phase of the ligand manufacturing process to address the issue of acidic impurities and storage stability of the resulting solid ligand. Likewise, U.S. Pat. No. 7,629,484 teaches treating the crude phosphite with extremely strong bases including strongly basic ion exchange resins at the last stages of production to remove all traces of acid formed during the ligand manufacture. U.S. Pat. No. 4,116,926 teaches the use of alkanolamine additives to prevent hydrolysis of phosphites used as polymer antioxidants but once exhausted, the degradation can still proceed.

In addition, a number of patents teach the use of ion exchange resins to remove impurities from transition metal-ligand solutions.

There remains a need for a simple process to produce phosphites of exceptionally low acid content to assure long-term storage stability, as well as a facile means of reprocessing partially degraded phosphites that contain high levels of phosphorous acid.

SUMMARY

We have found that the long-term storage stability of organophosphites is greatly influenced by the phosphorous acid content of the material at the time it is packaged, and that manufacturing processes that employ water or water/amine extraction to remove acidic impurities often leave significant amounts of residual phosphorous acid in the final product. The resulting product is susceptible to subsequent degradation upon storage. Surprisingly, it has been discovered that embodiments of the present invention reduce the phosphorous acid content of organophosphites to extremely low levels, and moreover, that the organophosphite thus produced is exceptionally stable during long-term storage. Embodiments of the present invention may also be utilized to remove phosphorous acid from phosphites that have partially degraded over time due to improper preparation, packaging or storage.

In one embodiment, a process of the present invention comprises (a) receiving a solid organophosphite compound that has been recrystallized or triturated, wherein the solid organophosphite compound comprises phosphorous acid; (b) dissolving the solid organophosphite compound in an organic solvent; (c) treating the solution with a weakly basic adsorbent; and collecting the treated organophosphite solution, wherein the acid content of the organophosphite following step (d) is 30 ppm or less.

DETAILED DESCRIPTION

In one aspect, a process of the present invention comprises receiving a solid organophosphite compound that has been recrystallized or triturated and that includes phosphorous acid. The solid organophosphite compound is dissolved in an organic solvent, and then treated with a weakly basic adsorbent. The solution is treated with a weakly basic adsorbent resulting in an organophosphite having an acid content of 30 ppm or less. In some embodiments, the acid content of the resulting organophosphite is 10 ppm or less. The acid content of the resulting organophosphite is 5 ppm or less in some embodiments.

In some embodiments, the weakly basic adsorbent comprises a weakly basic ion exchange resin. The weakly basic ion exchange resin comprises at least 10 equivalents of a basic moiety per mole of acid in the organophosphite solution in some embodiments. In some embodiments, the weakly basic adsorbent comprises a metal oxide, a metal carbonate, or an anionic clay having an effective $pK_a$ of less than 12.

The solid organophosphite compound is dissolved in the organic solvent in the absence of free amine in some embodiments. The solvent, in some embodiments, comprises toluene, xylenes, diethyl ether, dichloromethane, ethyl acetate, butyraldehyde, valeraldehyde, and butyraldehyde/butyraldehyde heavies mixtures, or mixtures thereof. In some embodiments, the solvent comprises an aromatic hydrocarbon. The solution that is treated with the weakly basic adsorbent, in some embodiments, comprises an aldehyde.

One would expect acid-base chemistry to be essentially instantaneous, but surprisingly it has been discovered that the acid content of an organophosphite compound may be greatly reduced by employing specific combinations of solid adsorbent and solvent, providing that the contacting is conducted for a significant period of time, generally more than 10 minutes. The reduction is not essentially instantaneous, even in the presence of large amounts of weakly basic adsorbent, but rather slow, yet still very effective. Thus, in some embodiments, the solution is treated with the weakly basic adsorbent for at least 10 minutes. The solution is treated with the weakly basic adsorbent for at least 120 minutes in some embodiments. In some embodiments, the solution is treated with the weakly basic adsorbent for up to 480 minutes. The solution is treated with the weakly basic adsorbent between 10 and 480 minutes in some embodiments. The solution is treated with the weakly basic adsorbent, in some embodiments, between 120 and 480 minutes.

In some embodiments, the solution is treated with the weakly basic adsorbent at a temperature of at least 20° C. The solution is treated with the weakly basic adsorbent at a temperature of at least 45° C. in some embodiments. The solution, in some embodiments, is treated with the weakly basic adsorbent at a temperature of 20° C. to 30° C.

In some embodiments, the solution is treated with the weakly basic adsorbent for at least 120 minutes at a temperature of 20° C. to 30° C. The solution is treated for at least 10 minutes at a temperature of at least 45° C. in some embodiments.

In some embodiments, treating the solution comprises transporting the solution through a bed comprising the adsorbent. Treating the solution, in some embodiments, comprises transporting the solution through a column comprising the adsorbent. Treating the solution comprises stirring a slurry of adsorbent in the solution in some embodiments.

In some embodiments, a process of the present invention further comprises removing the adsorbent by filtration.

In some embodiments, the process further comprises (e.g., after treatment with the weakly basic adsorbent) concentrating the organophosphite in the treated organophosphite solution, combining the concentrated organophosphite solution with an anti-solvent, and collecting the resulting solids. In some such embodiments, the organophosphite solution is concentrated to a residual organic solvent content of 50% by weight or less. In some embodiments, the process further comprises storing the resulting solids for at least 30 days, wherein the stored resulting solids comprise 25 ppm or less phosphorous acid after 30 days. In some embodiments where anti-solvent is combined with the concentrated organophosphite, the anti-solvent can be added to the concentrated organophosphite. Examples of anti-solvent that can be used in some such embodiments include isopropanol and t-butanol.

In some embodiments, after the removal of the acidic species by treatment with the weakly basic adsorbent, 0.05 to 13 acid-neutralizing equivalents per 100 moles ligand of an acid-scavenger is added to the solid organophosphite compound.

The organophosphite compound, in some embodiments, comprises at least one of the following:

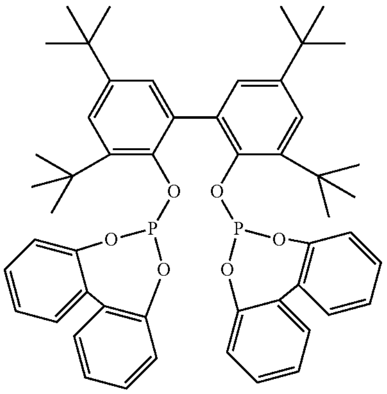

-continued

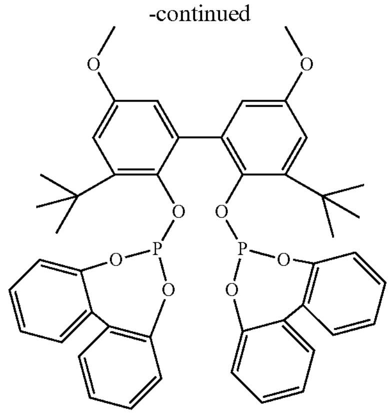

The organophosphite collected according to some embodiments of the present invention can be provided to a hydroformylation process. In some embodiments, the solid organophosphite compound that is provided at the beginning of some embodiments of processes of the present invention comprises a phosphorous acid that has been stored for at least 30 days.

All references to the Periodic Table of the Elements and the various groups therein are to the version published in the CRC Handbook of Chemistry and Physics, 72nd Ed. (1991-1992) CRC Press, at page I-11.

Unless stated to the contrary or implicit from the context, all parts and percentages are based on weight and all test methods are current as of the filing date of this application. For example, unless otherwise stated to the contrary, when relative amounts are provided as "parts per million", "ppm", "parts per billion", "ppb", or "parts" such amounts are on the basis of mass. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

Unless stated to the contrary or implicit from the context, all procedures described herein should be conducted under air-free conditions. Any suitable means to achieve air-free conditions (e.g. purging of systems with nitrogen or argon, etc.) may be employed.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "hydroformylation" is contemplated to include, but is not limited to, all processes that involve converting one or more olefinic compounds to one or more aldehydes using carbon monoxide, hydrogen, and a catalyst comprised of a transition metal and an organophosphite ligand.

As used herein, the term "mix tank" is contemplated to include a vessel that is used to mix organophosphite, and optionally weakly basic adsorbent, with a solvent to prepare an organophosphite solution. This vessel is generally not part of the hydroformylation reaction zone.

For purposes of this invention, the term "organic solvent" is contemplated to include all permissible organic compounds in which the organophosphite is soluble and stable and the adsorbent is insoluble and stable. Examples of representative organic solvents include aromatic hydrocarbons such as toluene and xylenes, dialkyl ethers such as diethyl ether, dichloromethane, alkyl acetate esters such as ethyl acetate, aldehydes such as butyraldehyde and valeraldehyde, and mixtures of aldehydes and aldehyde self-condensation products (also known as aldehyde "heavies"), such as butyraldehyde-butyraldehyde trimer mixtures, and the like. As used herein, the term "anti-solvent" is contemplated to comprise polar solvents and mixtures thereof that are incapable of dissolving appreciable amounts of the solid hydrolyzable organophosphite. Suitable anti-solvents have dielectric constants above 15 $\varepsilon_r(\omega)$ (at 20° C.) yet are still miscible with the organic solvent. Examples include acetonitrile and alcohols, such as isopropanol, tertiary butanol, and the like. The anti-solvent is employed to facilitate crystallization of the organophosphite or as a trituration solvent.

As used herein, the term "trituration" describes a process wherein organophosphite or a concentrate comprising organophosphite and organic solvent is combined with an anti-solvent and mixed thoroughly. In contrast to a recrystallization, a trituration does not involve appreciable dissolution of the organophosphite, but rather comprises slurrying the organophosphite in an anti-solvent. The trituration may be conducted using varying proportions of anti-solvent relative to organophosphite and at different temperatures.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, in which the number of carbons can range from 1 to 20 or more, preferably from 1 to 12, as well as hydroxyl and halogen. The permissible substituents can be one or more and the same or different for appropriate organic compounds. This invention is not intended to be limited in any manner by the permissible substituents of organic compounds.

Hydrolyzable organophosphorous ligands are trivalent phosphorous compounds that contain at least one P—Z bond wherein Z is oxygen, nitrogen, chlorine, fluorine or bromine. Organophosphites are a type of hydrolyzable organophosphorous ligand that is a trivalent phosphorous compound that contains at least one P—Z bond wherein Z is oxygen. Examples of hydrolyzable organophosphorous ligands include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligand may include chelate structures and/or may contain multiple P—Z moieties such as polyphosphites, polyphosphoramidites, etc. and mixed P—Z moieties such as phosphite-phosphoramidites, flurophosphite-phosphites, and the like. Examples of phosphite ligands include monoorganophosphite, diorganophosphite, triorganophosphite and organopolyphosphite compounds. Such organophosphorous compounds and methods for their preparation are well known in the art. Mixtures of hydrolyzable organophosphorous ligands can be employed.

Representative monoorganophosphites may include those having the formula:

<<I>>

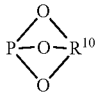

wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane and the like. Such monoorganophosphites may be found described in greater detail, for example, in U.S. Pat. No. 4,567,306.

Representative diorganophosphites may include those having the formula:

<<II>>

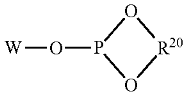

wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, and cycloalkylene radicals. The more preferred divalent acyclic radicals are the divalent alkylene radicals such as disclosed more fully, for example, in U.S. Pat. Nos. 3,415,906 and 4,567,302. Illustrative divalent aromatic radicals include, for example, arylene, bisarylene, arylene-alkylene, arylene-alkylene-arylene, arylene-oxy-arylene, arylene-S-arylene, arylene-S-alkylene, and the like. More preferably $R^{20}$ is a divalent aromatic radical such as disclosed more fully in, for example, U.S. Pat. Nos. 4,599,206, 4,717,775, and 4,835,299.

Representative of a more preferred class of diorganophosphites are those of the formula:

<<III>>

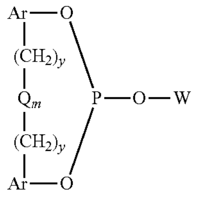

wherein W is as defined above, each Ar is the same or different and represents a substituted or unsubstituted aryl radical, each y is the same or different and is a value of 0 or 1, Q represents a divalent bridging group selected from $—C(R^{33})_2—$, —O—, —S—, $Si(R^{35})_2$ and —O—, wherein each $R^{33}$ is the same or different and represents hydrogen, an alkyl radical having from 1 to 12 carbon atoms, phenyl, tolyl, and anisyl, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

<<IV>>

wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl) phenylphosphite, bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

<<V>>

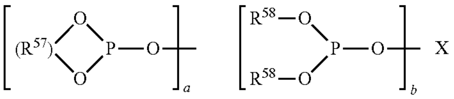

wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, arylene-$(CH_2)_y$-$Q_m$-$(CH_2)_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616; 5,364,950; and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

<<VI>>

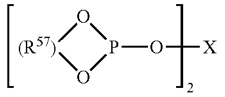

<<VII>>

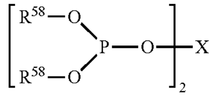

<<VIII>>

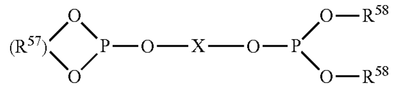

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite compounds of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or $—C(R^{35})_2—$ where each $R^{35}$ is the same or different and represents hydrogen or a methyl radical. More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by $—(CH_2)_y-(Q)_m-(CH_2)_y—$ is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as $—Si(R^{35})_3$; phosphine radicals such as $-aryl-P(R^{15})_2$; alkoxy radicals such as $—OR^{15}$; phosphonyl radicals such as $—P(O)(R^{15})_2$, as well as halo, trifluoromethyl, and the like, wherein each $R^{15}$ radical individually represents the same or different monovalent hydrocarbon radical having from 1 to 18 carbon atoms (e.g., alkyl, aryl, aralkyl, alkaryl and cyclohexyl radicals). It is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl, and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, $—OCH_2CH_2OCH_3$, $—O(CH_2CH_2)_2OCH_3$, $—O(CH_2CH_2)_3OCH_3$, and the like; aryloxy radicals such as phenoxy and the like; as well as silyl radicals such as $—Si(CH_3)_3$, $—Si(OCH_3)_3$, $—Si(C_3H_7)_3$, and the like; arylphosphine radicals such as $—P(C_6H_5)_2$ and the like; sulfinyl radicals such as $—S(O)CH_3$ and the like; sulfidyl radicals such as $—SCH_3$, $—SC_2H_5$, $—SC_6H_5$, and the like; phosphonyl radicals such as $—P(O)(C_6H_5)_2$, $—P(O)(CH_3)_2$, $—P(O)(C_2H_5)_2$, $—P(O)(C_3H_7)_2$, $—P(O)(C_4H_9)_2$, $—P(O)(C_6H_{13})_2$, $—P(O)CH_3(C_6H_5)$, $—P(O)(H)(C_6H_5)$, and the like.

Specific illustrative examples of such organophosphite compounds include the following: 2-t-butyl-4-methoxyphenyl(3,3'-di-t-butyl-5,5'-dimethoxy-1,1'-biphenyl-2,2'-diyl) phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3', 5,5'-tetrakis-tert-butyl-1,1-biphenyl)]-2,4-pentyldiphosphite, (2R, 4R)di[2,2'-(3,3'-di-tert-butyl-5,5'-dimethoxy-1,1'-biphenyl)]-2,4-pentyldiphosphite, 2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis[2-(1,1-dimethylethyl)-4-methoxyphenyl]ester of phosphorous acid.

Hydrolyzable organophosphorous ligands and general methods for their manufacture are well-known to those skilled in the art. In general, hydrolyzable organophosphorous ligands are produced by the reaction of $PCl_3$ with H—Z compounds, where Z is as defined herein, in the presence of a base (usually an amine or amine resin). The actual synthetic route to the crude hydrolyzable organophosphorous ligand prior to the steps described herein is not a critical feature of the invention.

In one aspect, the invention comprises a solid organophosphite composition that is substantially free of amine. Recrystallizing or triturating the crude hydrolyzable organophosphite ligand in a suitable solvent at least once prior to the process of the invention is required to assure that the organophosphite employed in the invention is substantially free of amine. Solvents known to be suitable for the initial recrystallization of organophosphite ligands may be found for example in WO2013066712 and WO2013098370. Examples of preferred recrystallization solvents include ethyl acetate, isopropyl acetate, propyl acetate, toluene and acetone. Solvents suitable for trituration comprise anti-solvents, such as acetonitrile and alcohols, including isopropanol, t-butanol and the like. The term “substantially free of amine” is contemplated to comprise a solid organophosphite composition that has been recrystallized or triturated at least once in a suitable solvent.

The organic solvent should be capable of dissolving the organophosphorous ligand and will typically have a dielectric constant less than 15 $\varepsilon_r(\omega)$. Examples of preferred organic solvents include toluene, dichloromethane, ethyl acetate, butyraldehyde, and butyraldehyde-butyraldehyde heavies mixtures, and the like. The amount of organic solvent employed is not critical, but should be sufficient to dissolve substantially all of the ligand at the treatment temperature. Advantageously, the treatment temperature is from 20° C. up to the boiling point of the solvent. In one aspect, the invention comprises dissolving a solid hydrolyzable organophosphite ligand in an organic solvent in the absence of free amine, treating the solution with a basic adsorbent, and then separating the solution from the adsorbent such that the resulting solution contains less than 30 ppm phosphorus acid, based on the mass of organophosphite. The separation can be done by passing the solution through a bed of adsorbent or stirring a slurry of adsorbent in the solution followed by filtration or decantation to remove the adsorbent, using techniques familiar to those skilled in the art.

In one aspect, the invention comprises dissolving a solid hydrolyzable organophosphite ligand in an organic solvent, and then treating the solution with a weakly basic solid adsorbent which selectively removes the acid moieties without removing or reacting with the phosphite. In some embodiments, the solid hydrolyzable organophosphite ligand is dissolved in an organic solvent in the absence of free amine. The adsorbent is largely insoluble in the solvent used to dissolve the organophosphite. The weakly basic solid adsorbent has an effective pKa of less than 12, preferably less than 10, and most preferably less than 8. In some embodiments, the adsorbent comprises a weakly basic ion exchange resin. The adsorbents can include activated aluminas, caustic alumina, silicas, anionic clays, resin-bound amines, and mixtures thereof. Resin bound amines are particularly useful in some embodiments. In general, preferred ion exchange resins are weakly basic, macro-porous or macro-reticular materials with primary, secondary, or tertiary amine moieties without substantial amounts of hydroxide ion present; tertiary amine-terminated resins are preferred when the organic solvent is butyraldehyde, butyraldehyde-butyraldehyde heavies mixtures, or the like. Suitable ion exchange resins include Amberlite IRA-67, Amberlite IRA-96, Amberlyst A21 (commercially available from The Dow Chemical Company), and the like. In some embodiments, more than one ion exchange resin, as well as mixed acid/base resins, can also be used, especially in cases where strongly alkaline reagents are employed in the organophosphite preparation or when resin or adsorbent leaching is a concern. For example, in some such embodiments, a bed of weakly basic ion exchange resin followed by a mixed acid/base resin may be employed. Insoluble inorganic salts can also be used as the solid adsorbent such as $NaHCO_3$, $KHCO_3$, $CaCO_3$, dibasic phosphates (Na or K), hydrotalcites, aluminates, and the like. Strong bases such as NaOH, KOH, and the like with pKa greated than 12 should not be used since they can degrade the organophosphite, generate side reactions with many solvents (e.g., react with aldehydes to form aldehyde heavies), and traces left in the product may have deleterious effects in the downstream uses as discussed above.

In some embodiments, the treatment may be performed as a slurry operation followed by filtration or decantation. In some embodiments, the treatment is performed in a column wherein the solution is passed through a column or bed of the adsorbent. This operation can be done in a batch mode or in continuous operation, and optionally can be done in a recycle operation until analysis of the purified organophosphite solution reveals sufficient acid removal has been accomplished. Persons of skill in the art can determine the appropriate treatment operation for their particular need using techniques known to those of skill in the art based on the teachings herein.

In one embodiment, the initially produced phosphite (after the conventional water extraction and subsequent recrystallization) can be redissolved in the organic solvent and treated with the adsorbent. The initial recrystallization removes the free amine and most of the other impurities such that the subsequent treatment with the adsorbent is not compromised by large amounts of such impurities.

In embodiments where a filtration step follows treatment with an adsorbent, the filtration to remove the adsorbent should employ as fine of a filter as practical and filter aids and body aids (celites, etc.) may be employed to enhance filter efficiency.

In one aspect of the invention, the acid-free organophosphite solution is concentrated by removing a portion of the organic solvent. Various means of facilitating solvent removal via vacuum, or under a flow of inert gas at elevated temperatures are known to the skilled person. A preferred method is to place the solution under vacuum at moderate temperature. In general it is desirable to remove as much of the organic solvent as practical. The solvent thus removed may be recycled in the case of continuous operation.

In one embodiment, the concentrated solution comprising organophosphite and organic solvent is transferred to a second vessel containing an anti-solvent. In such an embodiment, the volume of organic solvent should not be reduced beyond the solubility limit of the organophosphite. In other words, effectively transferring the concentrated solution comprising the organophosphite and organic solvent to a second vessel, requires that the organophosphite remain in solution. The temperature at which the transfer takes place will, to a large degree, dictate the amount of organic solvent that may be removed during the concentration step.

In a preferred embodiment, the organic solvent is substantially removed to leave the concentrate comprising organophosphite and organic solvent as a solid or slush. Although the amount of organic solvent remaining in the concentrate is not critical, advantageously a mixture of approximately 50:50 by weight organophosphite and organic solvent is achieved. In such an embodiment, an anti-solvent is transferred to the vessel containing the concentrate comprising the organophosphite and organic solvent.

In one aspect the concentrate comprising the organophosphite and organic solvent is combined and mixed with an anti-solvent. The volume of anti-solvent should be equal to or greater than the volume of the concentrate comprising the organophosphite and organic solvent (e.g. at least 1 part of anti-solvent for every part of concentrate), and in some cases a large excess of anti-solvent may be employed. Once combined, the mixture may advantageously be heated with agitation to >65° C. for an hour or more to obtain a solid that will dry quickly as described in PCT Publication No. WO2013/066712. The resulting solid phosphite should then be collected (e.g. via filtration or centrifugation), washed with a portion of the anti-solvent and dried. The particular methods of such filtration, washing and drying are not critical, and exemplary methods have been described previously in PCT Publication No. WO2013066712.

The invention is also useful to reprocess partially degraded material that has generated phosphorous acid during storage. In one embodiment, the partially degraded organophosphite is dissolved in a mix tank. In this case, the solid organophosphite is added to the mix tank and then air is removed, e.g., via $N_2$ purge or vacuum/$N_2$ refill, prior to charging the solvent to avoid oxidation of the ligand. Optionally the adsorbent may be added along with the solid organophosphite. In a preferred embodiment, the solvent comprises aldehyde or mixtures of aldehyde and aldehyde self-condensation products. Once the desired components are present, the mixing can be achieved according to methods, and using equipment, well known to those skilled in the art. For example, the mixing may be conducted in a simple stirred tank that is not subject to the pressures and temperatures found in reaction vessels. Agitation may be provided by circulation induced by an agitator, a pump, or other known agitation means. In various embodiments of the invention, the ligand solution comprises, consists essentially of, or consists of, the hydrolyzable organophosphorous ligand, the solvent, and the adsorbent.

In one embodiment of the invention, a preliminary solution of the partially degraded organophoshite and the solvent is prepared, and then circulated through a fixed bed comprised of the adsorbent. The circulation may be conducted until such time as the phosphorous acid content of the organophosphite is reduced to <30 ppm. The organophosphite solution thus obtained may then be added directly to a hydroformylation process.

The resulting low phosphorous acid solution is then concentrated, combined with the anti-solvent and processed as above.

Optionally an acid scavenger may be added which is a compound that serves to further increase the storage stability of the hydrolyzable organophosphorous ligand as described in PCT Application Serial No. PCT/US2015/026648). The optional acid scavenger is preferably added during the final step of the invention or is admixed with solid hydrolyzable organophosphorous ligand before or during packaging. When the optional acid scavenger is added to the anti-solvent, the amount of acid scavenger is between 0.01 and 1 wt %, more preferably between 0.05 and 0.5 wt % of the total solution.

Some embodiments of the present invention will now be described in detail in the following Examples.

EXAMPLES

All parts and percentages in the following examples are by weight unless otherwise indicated. All manipulations are done in a $N_2$-glove box or via Schlenk techniques to exclude air and moisture unless otherwise indicated. Solid Ligand A is used in the following examples:

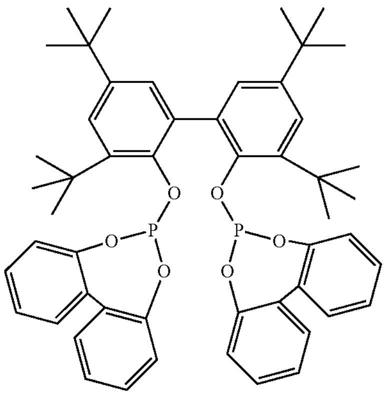

Ligand A

Phosphorous acid content of solid Ligand A is determined by ion chromatography (IC) using a Dionex ICS 2100 ion chromatograph with eluent generation and suppressed conductivity detection including a carbonate removal device. The chromatograph is fitted with an IonPac AG11-HC Guard Column and an IonPac AS11-HC Analytical Column. Data analysis is performed with Chromeleon 7.0 software. Unless otherwise indicated, samples are prepared by dissolution of the solid ligand (0.1 to 0.5 g) in toluene (5-10 mL) followed by extraction of the toluene solution with deionized water (8-15 mL). Phosphorous acid quantitation is reported as part per million by weight in the organophosphite. Samples containing very high levels of acid require additional dilution of the aqueous extract to stay within the calibration range. Unless otherwise indicated, Ligand A used herein is not crude material but has previously been purified via recrystallization as described, for example, in PCT Publication No. WO2013/066712. Weakly basic ion exchange resins Amberlite IRA96 and IRA67 (free base, wet) were purchased from Aldrich and used without modification. The "Amine:phosphorous acid (molar)" ratio was calculated based on the reported ion exchange capacity (meq/mL) of each resin on a wet volume basis and the known level of phosphorous acid in a particular organophosphite sample. Basic alumina (Brockmann I, 150 mesh) and sodium carbonate were purchased from Aldrich and used without modification. After treatment of the organophosphite solution with the specified weakly basic adsorbent, the resulting purified organophosphite solution was removed using a syringe and transferred to a glass vial for extraction with deionized water for IC analysis.

Examples 1-4

Solid Ligand A (0.25 g) containing 1248 ppm phosphorous acid is weighed into 20 mL glass vials and dissolved in the specified organic solvent (6.5-12.0 g). The solution is treated with 0.5 g Amberlite IRA96 weakly basic resin (free base, wet resin) and the resulting suspension is magnetically stirred at ambient temperature for 2 hours. The supernatant is removed and extracted with deionized water (8.0 g); the aqueous layer is analyzed by IC. The results are summarized in Table 1.

TABLE 1

Purification of Ligand A using Weakly Basic Resin.

| | solvent | amine: phosphorous acid (molar) | post-treatment phosphorous acid (ppm) |
|---|---|---|---|
| Example 1 | toluene | 271 | 1.6 |
| Example 2 | 3:1 butyraldehyde: texanol | 285 | 15.4 |
| Example 3 | dichloromethane | 283 | 7.7 |
| Example 4 | ethyl acetate | 319 | 12.5 |

Comparative Experiments A-B

Solid Ligand A (0.25 g) containing 1248 ppm phosphorous acid is weighed into 20 mL glass vials and dissolved in the specified organic solvent (6.5-12.0 g). The solution is treated with 0.5 g Amberlite IRA96 weakly basic resin (free base, wet resin) and the resulting suspension is magnetically stirred at ambient temperature for the indicated time. The supernatant is removed and extracted with deionized water (8.0 g); the aqueous layer is analyzed by IC. The results are summarized in Table 2.

TABLE 2

Impact of Treatment Time on Purification of Ligand A using Weakly Basic Resin.

| | treatment time (min) | solvent | amine: phosphorous acid (molar) | post-treatment phosphorous acid (ppm) |
|---|---|---|---|---|
| Comparative Experiment A | 10 | toluene | 294 | 742.0 |
| Comparative Experiment B | 10 | 3:1 butyraldehyde: texanol | 307 | 200.3 |

The examples summarized in Table 2 show that briefly contacting the solutions with the adsorbent is not sufficient to achieve the desired result.

Examples 5-6

Solid Ligand A (0.25 g) containing 1248 ppm phosphorous acid is weighed into 20 mL glass vials and dissolved in the specified organic solvent (6.5-12.0 g). The solution is treated with 0.5 g Amberlite IRA96 weakly basic resin (free base, wet resin) and the resulting suspension is magnetically stirred at 60° C. for 2 hours. The supernatant is removed and extracted with deionized water (8.0 g); the aqueous layer is analyzed by IC. The results are summarized in Table 3.

TABLE 3

Purification of Ligand A using Weakly Basic Resin at 60° C.

| | solvent | amine: phosphorous acid (molar) | post-treatment phosphorous acid (ppm) |
|---|---|---|---|
| Example 5 | toluene | 295 | 7.9 |
| Example 6 | 3:1 butyraldehyde: texanol | 311 | 6.5 |

Comparative Experiments C-E and Examples 7-8

Solid Ligand A (0.25 g) containing 10,200 ppm phosphorous acid is weighed into 20 mL glass vials and dissolved in the specified organic solvent (6.5-12.0 g). The solution is treated with 0.5 g Amberlite IRA96 weakly basic resin (free base, wet resin) and the resulting suspension is magnetically stirred at ambient temperature for the indicated time. The supernatant is removed and extracted with deionized water (8.0 g); the aqueous layer is analyzed by IC. The results are summarized in Table 4.

TABLE 4

Impact of Treatment Time on Purification of Ligand A using Weakly Basic Resin.

| | treatment time (min) | solvent | amine: phosphorous acid (molar) | post-treatment phosphorous acid (ppm) |
|---|---|---|---|---|
| Comparative Experiment C | 10 | toluene | 30 | 801.9 |
| Example 7 | 120 | toluene | 30 | 8.0 |
| Comparative Experiment D | 10 | 3:1 butyraldehyde: texanol | 32 | 1429.2 |
| Comparative Experiment E | 120 | 3:1 butyraldehyde: texanol | 33 | 60.8 |
| Example 8 | 360 | 3:1 butyraldehyde: texanol | 32 | 35.5 |

These examples show that organophosphites of exceptionally high acid content may be effectively treated with the present invention. Moreover the results of Table 4 highlight that contact time must be considered when selecting treatment conditions (i.e., along with beginning acid content and combinations of solvents and weakly basic adsorbents). Example 8 is clearly approaching the desired specification limit and merely requires an additional bed, more adsorbent, or slightly longer contact to achieve the 30 ppm limit starting from an extremely degraded material.

Examples 9-10

Solid Ligand A (0.25 g) containing 10,200 ppm phosphorous acid is weighed into 20 mL glass vials and dissolved in the specified organic solvent (6.5-12.0 g). The solution is treated with 0.5 g Amberlite IRA67 weakly basic gellular resin (free base, wet resin) and the resulting suspension is magnetically stirred at ambient temperature for the indicated time. The supernatant is removed and extracted with deionized water (8.0 g); the aqueous layer is analyzed by IC. The results are summarized in Table 5.

TABLE 5

Purification of Ligand A using Weakly Basic Gellular Resin.

| | treatment time (min) | solvent | amine: phosphorous acid (molar) | post-treatment phosphorous acid (ppm) |
|---|---|---|---|---|
| Example 9 | 120 | toluene | 38 | 2.9 |
| Example 10 | 360 | 3:1 butyraldehyde: texanol | 39 | 30 |

The examples of Table 5 show that a weakly basic gellular resin is quite effective.

Examples 11-12

Solid Ligand A (0.25 g) containing 1248 ppm phosphorous acid is weighed into 20 mL glass vials and dissolved in toluene (6.5 g). The solution is treated with 0.5 g specified basic adsorbent and the resulting suspension is magnetically stirred at ambient temperature for 2 hours. The supernatant is removed (syringe filter used to remove fine adsorbent particles) and extracted with deionized water (8.0 g); the aqueous layer is analyzed by IC.

The results are summarized in Table 6.

TABLE 6

Impact of Type of Basic Adsorbent on Purification of Ligand A.

| | basic adsorbent | solvent | post-treatment phosphorous acid (ppm) |
|---|---|---|---|
| Example 11 | basic alumina | 3:1 butyraldehyde: texanol | 5.8 |
| Example 12 | sodium carbonate | 3:1 butyraldehyde: texanol | 6.9 |

These results show that alternative adsorbents may be effectively employed.

Comparative Experiment F and Examples 13-15

Solid Ligand A (0.25 g) containing 1248 ppm phosphorous acid is weighed into 20 mL glass vials and dissolved in toluene (6.5 g). The solution is treated with 0.02, 0.05, 0.10, or 0.25 g Amberlite IRA96 weakly basic resin (free base, wet resin) and the resulting suspension is magnetically stirred at ambient temperature for the indicated time. The supernatant is removed and extracted with deionized water (8.0 g); the aqueous layer is analyzed by IC. The results are summarized in Table 7.

TABLE 7

Purification of Ligand A using Different Amounts of Weakly Basic Resin.

| | resin weight (g) | treatment time (mm) | solvent | amine phosphorous acid (molar) | post-treatment phosphorous acid (Ppm) |
|---|---|---|---|---|---|
| Comparative Experiment F | 0.02 | 120 | toluene | 11:1 | 57.5 |

TABLE 7-continued

Purification of Ligand A using Different Amounts of Weakly Basic Resin.

| | resin weight (g) | treatment time (mm) | solvent | amine phosphorous acid (molar) | post-treatment phosphorous acid (Ppm) |
|---|---|---|---|---|---|
| Example 13 | 0.05 | 120 | toluene | 31:1 | 9.4 |
| Example 14 | 0.10 | 120 | toluene | 63:1 | 1.3 |
| Example 15 | 0.25 | 120 | toluene | 147:1 | 0.7 |

Examples 16-18

Solid Ligand A (0.25 g) containing 1248 ppm phosphorous acid is weighed into 20 mL glass vials and dissolved in freshly distilled butyraldehyde (6.5 g, contained 0.35 wt % aldehyde heavies). The solution is treated with 0.025, 0.050, or 0.125 g Amberlite IRA96 weakly basic resin (free base, wet resin) and the resulting suspension is magnetically stirred at ambient temperature for 5 hours. The supernatant is removed and extracted with deionized water (8.0 g); the aqueous layer is analyzed by IC. The results are summarized in Table 8.

TABLE 8

Purification of Ligand A using Different Amounts of Weakly Basic Resin in Butyraldehyde.

| | resin weight (g) | Treatment time (min) | solvent | amine: phosphorous acid (molar) | post-treatment phosphorous acid (ppm) | post-treatment wt % aldehyde heavies |
|---|---|---|---|---|---|---|
| Example 16 | 0.025 | 300 | C4 aldehyde | 15:1 | 16.4 | 0.49 |
| Example 17 | 0.05 | 300 | C4 aldehyde | 30:1 | 7.9 | 0.61 |
| Example 18 | 0.125 | 300 | C4 aldehyde | 80:1 | 8.9 | 0.74 |

The results of Table 8 show that the present invention may be effectively employed in a mix tank setting, wherein the organophosphite is dissolved in aldehyde prior to use in a continuous hydroformylation process. The weakly basic resins do not generate significant amounts of aldehyde heavies during this treatment.

What is claimed is:

1. A process comprising: (a) receiving a solid organophosphite compound that has been recrystallized or triturated, wherein the solid organophosphite compound comprises phosphorous acid; (b) dissolving the solid organophosphite compound in an organic solvent; and (c) treating the solution with a weakly basic adsorbent; and (d) collecting the treated organophosphite solution, wherein the acid content of the organophosphite following step (d) is 30 ppm or less.

2. The process of claim 1, wherein the weakly basic adsorbent comprises a metal oxide, a metal carbonate, or an anionic clay having an effective pKa of less than 12 or a weakly basic ion exchange resin.

3. The process of claim 2, wherein the weakly basic adsorbent comprises a weakly basic ion exchange resin, and the weakly basic ion exchange resin comprises at least 10 equivalents of a basic moiety per mole of acid in the organophosphite solution.

4. The process of claim 1, wherein the solid organophosphite compound is dissolved in the organic solvent in the absence of free amine.

5. The process of claim 1, wherein the solvent comprises toluene, xylenes, diethyl ether, dichloromethane, ethyl acetate, butyraldehyde, valeraldehyde, butyraldehyde/butyraldehyde heavies mixtures, valeraldehyde/valeraldehyde heavies mixtures or mixtures thereof.

6. The process of claim 1, wherein the solution is treated with the weakly basic adsorbent for at least 20 minutes at a temperature of 20° C. to 80° C.

7. The process of claim 1, wherein treating the solution comprises transporting the solution through a bed comprising the adsorbent.

8. The process of claim 1, further comprising (d) optionally filtering and concentrating the organophosphite in the treated organophosphite solution; (e) combining the concentration comprising the organic solvent and organophosphite with an anti-solvent; and (f) collecting the resulting solids.

9. The process of claim 8, further comprising (g) storing the resulting solids for at least 30 days, wherein the stored resulting solids comprise 25 ppm or less phosphorous acid after 30 days.

10. The process of claim 8, wherein the anti-solvent is added to the concentrated organophosphite in solution.

11. The process of claim 8, wherein the anti-solvent is isopropanol or t-butanol.

12. The process of claim 1, wherein the acid content of the organophosphite following step (d) is 10 ppm or less.

13. The process of claim 1, wherein the solid organophosphite compound comprising phosphorous acid has been stored for at least 30 days.

14. The process of claim 1, wherein from 0.05 to 13 acid-neutralizing equivalents per 100 moles organophosphite of an acid-scavenger is added to the product during or after step (d) collecting the treated organophosphite solution.

15. The process of claim 1, wherein the organophosphite compound comprises the following:

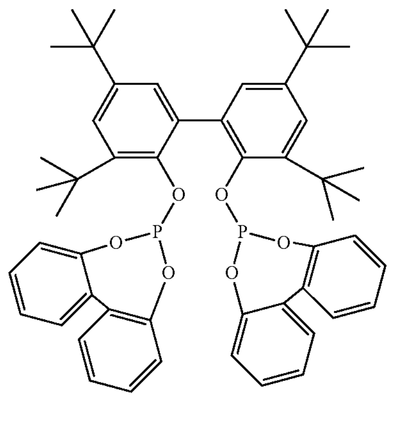

-continued
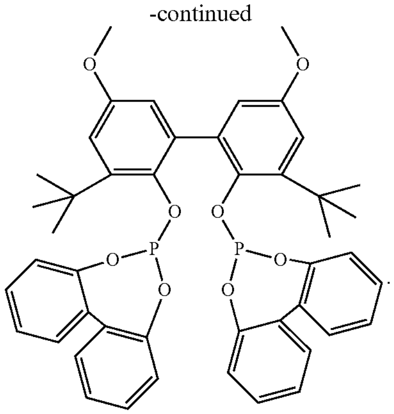
* * * * *